(12) United States Patent
Orszulak

(10) Patent No.: US 8,968,295 B2
(45) Date of Patent: Mar. 3, 2015

(54) ELECTROSURGICAL APPARATUS WITH HIGH SPEED ENERGY RECOVERY

(71) Applicant: TYCO Healthcare Group LP, Mansfield, MA (US)

(72) Inventor: James H. Orszulak, Nederland, CO (US)

(73) Assignee: Covidien LP, Mansfield, MA (US)

( * ) Notice: Subject to any disclaimer, the term of this patent is extended or adjusted under 35 U.S.C. 154(b) by 268 days.

(21) Appl. No.: 13/627,136

(22) Filed: Sep. 26, 2012

(65) Prior Publication Data

US 2013/0023869 A1 Jan. 24, 2013

Related U.S. Application Data

(63) Continuation of application No. 12/205,298, filed on Sep. 5, 2008, now Pat. No. 8,287,529.

(51) Int. Cl.
*A61B 18/04* (2006.01)
*A61B 18/18* (2006.01)

(52) U.S. Cl.
USPC .................. 606/34; 606/37; 606/38; 606/39; 606/40

(58) Field of Classification Search
USPC ............................... 606/34, 37–40
See application file for complete search history.

(56) References Cited

U.S. PATENT DOCUMENTS

| | | | |
|---|---|---|---|
| 3,641,422 A | 2/1972 | Farnsworth et al. | |
| 3,978,393 A | 8/1976 | Wisner et al. | |
| 4,767,999 A | 8/1988 | VerPlanck | |
| 5,694,304 A | 12/1997 | Telefus et al. | |
| 5,712,772 A | 1/1998 | Telefus et al. | |
| 5,836,943 A | 11/1998 | Miller, III | |
| 6,093,186 A | 7/2000 | Goble | |
| 6,238,387 B1 | 5/2001 | Miller, III | |
| 6,261,286 B1 | 7/2001 | Goble et al. | |
| 6,293,942 B1 | 9/2001 | Goble et al. | |
| 6,364,877 B1 | 4/2002 | Goble et al. | |

(Continued)

FOREIGN PATENT DOCUMENTS

DE 179607 3/1905
DE 390937 3/1924

(Continued)

OTHER PUBLICATIONS

U.S. Appl. No. 10/406,690, filed Apr. 3, 2003, Klicek.

(Continued)

*Primary Examiner* — Nicole F Lavert

(57) ABSTRACT

A circuit for controlling the discharging of stored energy in an electrosurgical generator includes a pulse modulator which controls an output of a power supply. At least one comparator is configured to provide an error signal to the pulse modulator based on a comparison between an output signal generated by the power supply and a feedback signal generated in response to the application of energy to tissue. A discharge circuit is configured to control the discharge of the output of the power supply to an inductive load disposed in parallel with the output of the power supply based on the comparison between the output signal and the feedback signal. The discharge circuit provides a rapid response and time rate control of the delivered electrosurgical energy by controlling the power supply and delivered RF energy in real time, based on a feedback signal generated in response to the application of energy to tissue.

10 Claims, 4 Drawing Sheets

(56) References Cited

U.S. PATENT DOCUMENTS

| | | | |
|---|---|---|---|
| 6,416,509 | B1 | 7/2002 | Goble et al. |
| 6,740,079 | B1 | 5/2004 | Eggers et al. |
| 6,923,804 | B2 * | 8/2005 | Eggers et al. ............ 606/34 |
| 8,162,932 | B2 | 4/2012 | Podhajsky et al. |
| 8,167,875 | B2 | 5/2012 | Podhajsky et al. |
| 8,180,433 | B2 | 5/2012 | Brannan et al. |
| 8,211,100 | B2 | 7/2012 | Podhajsky et al. |
| 8,226,639 | B2 | 7/2012 | Podhajsky et al. |
| 8,248,075 | B2 | 8/2012 | Brannan et al. |
| 8,257,349 | B2 | 9/2012 | Orszulak |
| 8,287,527 | B2 | 10/2012 | Brannan et al. |
| 8,287,528 | B2 | 10/2012 | Wham et al. |
| 8,287,529 | B2 | 10/2012 | Orszulak |
| 2005/0143725 | A1 | 6/2005 | Daners et al. |
| 2009/0234350 | A1 | 9/2009 | Behnke et al. |
| 2009/0254077 | A1 | 10/2009 | Craig |
| 2010/0057076 | A1 | 3/2010 | Behnke et al. |
| 2010/0063497 | A1 | 3/2010 | Orszulak |
| 2010/0082022 | A1 | 4/2010 | Haley et al. |
| 2010/0082024 | A1 | 4/2010 | Brannan et al. |
| 2010/0082025 | A1 | 4/2010 | Brannan et al. |
| 2010/0082083 | A1 | 4/2010 | Brannan et al. |
| 2010/0094271 | A1 | 4/2010 | Ward et al. |
| 2010/0094288 | A1 | 4/2010 | Kerr |
| 2010/0179533 | A1 | 7/2010 | Podhajsky |
| 2010/0179535 | A1 | 7/2010 | Podhajsky et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 880220 | 6/2006 |
| EP | 1645235 | 12/2006 |
| EP | 1776929 | 4/2007 |
| ER | 2517953 | 6/1983 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO 00/54683 | 9/2000 |

OTHER PUBLICATIONS

U.S. Appl. No. 11/242,458, filed Oct. 3, 2005, Becker et al.
U.S. Appl. No. 10/573,713, filed Mar. 28, 2006, Wham.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan. "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., Radiofrequency Lesion Generation and Its Effect on Tissue Impedance Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System", 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.

(56) References Cited

OTHER PUBLICATIONS

International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09169589 dated Mar. 2, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

* cited by examiner

ELECTROSURGICAL APPARATUS WITH HIGH SPEED ENERGY RECOVERY

CROSS-REFERENCE TO RELATED APPLICATIONS

This application is a continuation of U.S. patent application Ser. No. 12/205,298, now U.S. Pat. No. 8,287,529, filed on Sep. 5, 2008, entitled "ELECTROSURGICAL APPARATUS WITH HIGH SPEED ENERGY RECOVERY," the contents of which are incorporated by reference herein in their entirety.

BACKGROUND

1. Technical Field

The present disclosure relates to an electrosurgical system and method and, more particularly, to an electrosurgical generator configured to dynamically control energy output.

2. Background of Related Art

Electrosurgery involves application of high radio frequency electrical current to a surgical site to cut, seal, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of a surgical instrument held by the surgeon and applied to the tissue to be treated. A patient return electrode is placed remotely from the active electrode to carry the current back to the generator.

In bipolar electrosurgery, a hand-held instrument typically carries two electrodes, e.g., electrosurgical forceps. One of the electrodes of the hand-held instrument functions as the active electrode and the other as the return electrode. The return electrode is placed in close proximity to the active (i.e., current supplying) electrode such that an electrical circuit is formed between the two electrodes. In this manner, the applied electrical current is limited to the body tissue positioned between the two electrodes.

Conventional electrosurgical generators include a high voltage direct current power supply connected to a radio frequency (RF) output stage that converts DC energy generated by the power supply into RF energy. The power supply includes an output filter which substantially eliminates undesirable frequencies (e.g., noise) from the DC energy and stores large amounts of energy. Rapid tissue desiccation during the application of RF energy creates a potential for patient burn hazards due to excess energy dosage at the tissue site when the power source fails to rapidly alter the supplied energy dosage in response with dynamic changes in tissue impedance. Rising tissue impedance levels caused by desiccation unload the energy source and sustain the energy delivered to the tissue due to the large amount of stored energy in the output filter.

SUMMARY

According to one embodiment of the present disclosure, a circuit for controlling the discharging of stored energy in an electrosurgical generator includes a pulse modulator which controls an output of a power supply. At least one comparator is configured to provide an error signal to the pulse modulator based on a comparison between an output generated by the power supply and a feedback signal generated in response to the application of energy to tissue. A discharge circuit is configured to control the discharge of the output of the power supply to an inductive load disposed in parallel with the output of the power supply based on the comparison between the power supply output and the feedback signal.

According to another embodiment of the present disclosure, a circuit for controlling the discharging of stored energy in an electrosurgical generator includes a pulse modulator which controls an output of a power supply. At least one comparator is configured to provide an error signal to the pulse modulator based on a comparison between an output generated by the power supply and a feedback signal generated in response to the application of energy to tissue. A discharge circuit has a first switching component configured to discharge the output of the power supply to an inductive load disposed in parallel with the output of the power supply if the feedback signal is less than the power supply output and a second switching component configured to control switching of the first switching component based on the discharge rate of the output to the inductive load.

The present disclosure also provides a method for controlling the discharging of stored energy in an electrosurgical generator. The method includes applying energy stored in an output of a power supply to tissue. The method also includes generating at least one control signal based on at least one of a sensed tissue property and a sensed energy delivery property, (i.e. power, voltage, current, time etc.). The method also includes generating an error signal based on a comparison between the at least one control signal and the energy stored in the output. The method also includes discharging the stored energy to an inductive load in parallel with the output of the power supply based upon the comparison between the energy stored in the output and the control signal.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

In general, the present disclosure provides for an electrosurgical generator including a power supply configured to rapidly re-direct stored output energy through inductive energy transfer utilizing a controlled switching circuit to regulate, in real-time, the level of power sourced to the RF energy delivered to tissue during treatment.

More specifically, when the generator senses increased impedance in tissue due to rapid tissue desiccation, the generator of the present disclosure can control, in real time, the amount of treatment energy applied to tissue through use of a so-called "discharge" circuit. The discharge circuit provides a rapid response and time rate control of the electrosurgical energy delivered to tissue by discharging energy stored in an output filter of the power supply into an inductive load based on a feedback signal generated by the controller. The feedback signal may be based on a sensed tissue property (e.g., impedance) and/or an energy property (e.g., voltage, output energy level, etc.). This control provides for more accurate application of target treatment energy levels to treat tissue.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing, ablation).

Figure 1A:
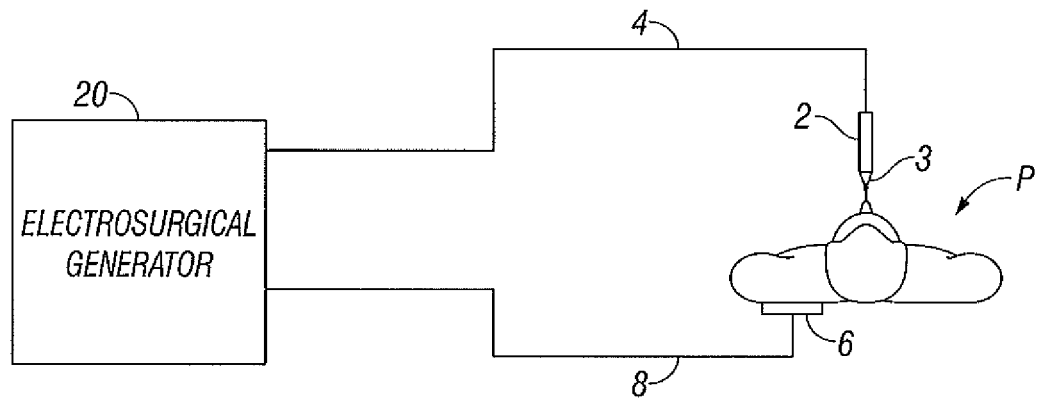
FIG. 1A is a schematic block diagram of a monopolar electrosurgical system in accordance with an embodiment of the present disclosure.

FIG. 1A is a schematic illustration of a monopolar electrosurgical system according to one embodiment of the present disclosure. The system includes a monopolar electrosurgical instrument 2 including one or more active electrodes 3, which can be electrosurgical cutting probes, ablation electrode(s), etc. Electrosurgical RF energy is supplied to the instrument 2 by a generator 20 via a supply line 4, which is connected to an active terminal 30 (FIG. 2) of the generator 20, allowing the instrument 2 to coagulate, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8, respectively.

Figure 1B:
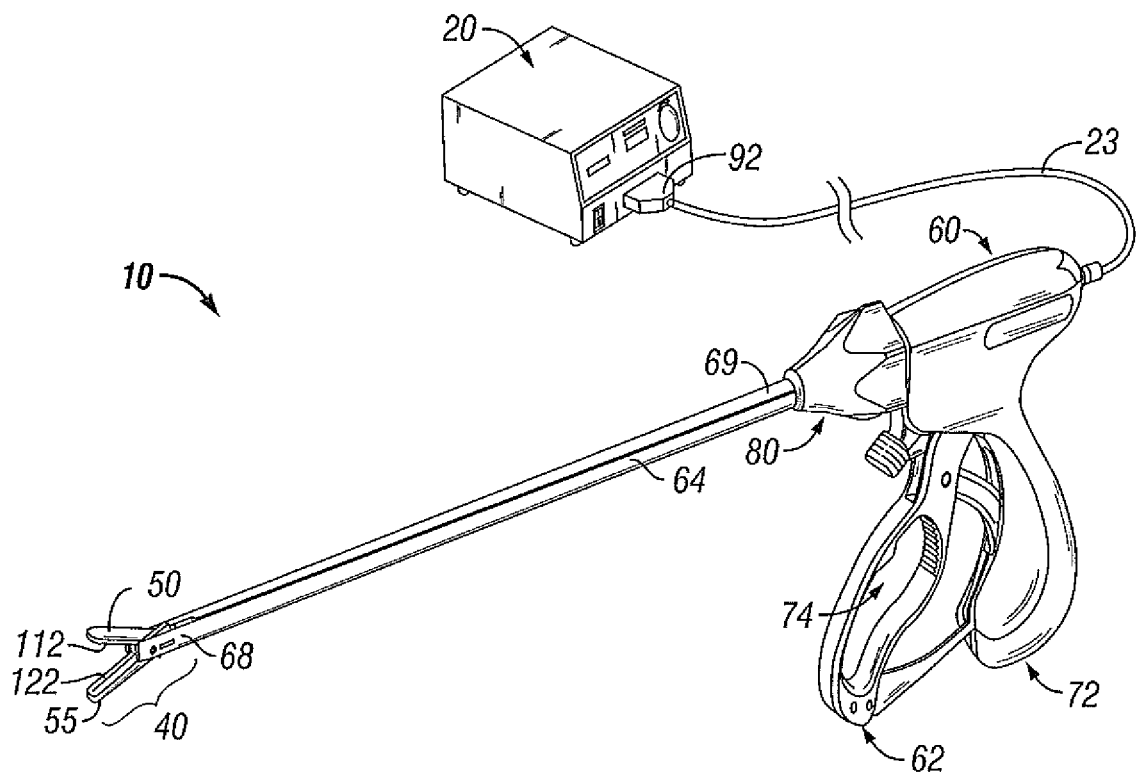
FIG. 1B is a schematic block diagram of a bipolar electrosurgical system in accordance with an embodiment of the present disclosure.

The present disclosure may be adapted for use with either monopolar or bipolar electrosurgical systems. FIG. 1B shows a bipolar electrosurgical system according to the present disclosure that includes an electrosurgical forceps 10 having opposing jaw members 50 and 55. The forceps 10 includes a shaft member 64 having an end effector assembly 40 disposed at the distal end thereof. The end effector assembly 40 includes two jaw members 50 and 55 movable from a first position wherein the jaw members 50 and 55 are spaced relative to another to a closed position wherein the jaw members 50 and 55 cooperate to grasp tissue therebetween. Each of the jaw members 50 and 55 includes an electrically conductive sealing plate 112 and 122, respectively, connected to the generator 20 that communicates electrosurgical energy through the tissue held therebetween.

Figure 2:
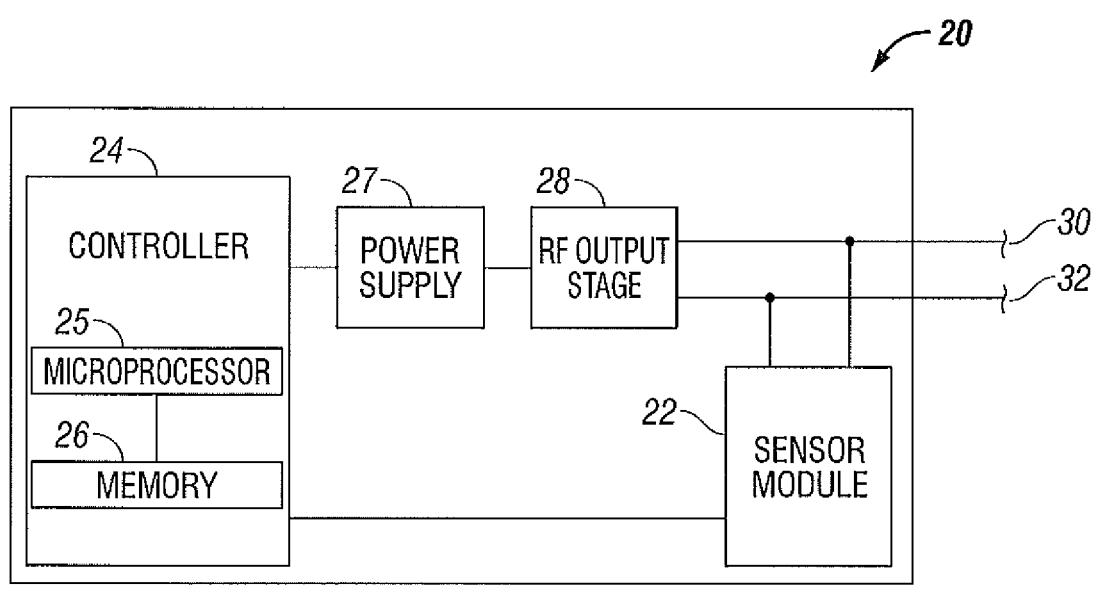
FIG. 2 is a schematic block diagram of a generator in accordance with an embodiment of the present disclosure.

Electrically conductive sealing plates 112 and 122, which act as active and return electrodes, are connected to the generator 20 through cable 23, which includes the supply and return lines coupled to the active and return terminals 30, 32 (FIG. 2). The electrosurgical forceps 10 is coupled to the generator 20 at the active and return terminals 30 and 32 (e.g., pins) via a plug 92 disposed at the end of the cable 23, wherein the plug includes contacts from the supply and return lines. Electrosurgical RF energy is supplied to the forceps 10 by generator 20 via a supply line connected to the active electrode and returned through a return line connected to the return electrode.

Forceps 10 generally includes a housing 60 and a handle assembly 74 that includes moveable handle 62 and handle 72 which is integral with the housing 60. Handle 62 is moveable relative to handle 72 to actuate the end effector assembly 40 to grasp and treat tissue. The forceps 10 also includes shaft 64 that has a distal end 68 that mechanically engages the end effector assembly 40 and a proximal end 69 that mechanically engages the housing 60 proximate a rotating assembly 80 disposed at a distal end of the housing 60.

With reference to FIG. 1B, the generator 20 includes suitable input controls (e.g., buttons, activators, switches, touch screen, etc.) for controlling the generator 20. In addition, the generator 20 includes one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., coagulating, tissue sealing, division with hemostasis, etc.). Further, the forceps 10 may include a plurality of input controls which may be redundant with certain input controls of the generator 20. Placing the input controls at the forceps 10 allows for easier and faster modification of RF energy parameters during the surgical procedure without requiring interaction with the generator 20.

FIG. 2 shows a schematic block diagram of the generator 20 having a controller 24, a power supply 27, an RF output stage 28, and a sensor module 22. The power supply 27 may provide DC power to the RF output stage 28 which then converts the DC power into RF energy and delivers the RF energy to the forceps 10. The controller 24 includes a microprocessor 25 having a memory 26 which may be volatile type memory (e.g., RAM) and/or non-volatile type memory (e.g., flash media, disk media, etc.). The microprocessor 25 includes an output port connected to the power supply 27 and/or RF output stage 28 which allows the microprocessor 25 to control the output of the generator 20 according to either open and/or closed control loop schemes.

A closed loop control scheme generally includes a feedback control loop wherein the sensor module 22 provides feedback to the controller 24 (i.e., information obtained from one or more sensing mechanisms that sense various tissue parameters such as tissue impedance, tissue temperature, output current and/or voltage, etc.). The controller 24 then signals the power supply 27, which then adjusts the DC power supplied to the RF output stage, accordingly. The controller 24 also receives input signals from the input controls of the generator 20 and/or forceps 10. The controller 24 utilizes the input signals to adjust the power output of the generator 20 and/or instructs the generator 20 to perform other control functions.

The microprocessor 25 is capable of executing software instructions for processing data received by the sensor module 22, and for outputting control signals to the generator 20, accordingly. The software instructions, which are executable by the controller 24, are stored in the memory 26 of the controller 24.

The controller 24 may include analog and/or logic circuitry for processing the sensed values and determining the control signals that are sent to the generator 20, rather than, or in combination with, the microprocessor 25.

The sensor module 22 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 24. The sensor module 22 may include control circuitry which receives information from multiple sensors, and provides the information and the source of the information (e.g., the particular sensor providing the information) to the controller 24.

More particularly, the sensor module 22 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

The measured or sensed values are further processed, either by circuitry and/or a processor (not explicitly shown) in the sensor module 22 and/or by the controller 24, to determine changes in sensed values and tissue impedance. Tissue impedance and changes thereto may be determined by measuring the voltage and/or current across the tissue and then calculating changes thereof over time. The measured and calculated values may be then compared with known or desired voltage and current values associated with various tissue types, procedures, instruments, etc. This may be used to drive electrosurgical output to achieve desired impedance and/or change in impedance values. As the surgical procedure proceeds, tissue impedance fluctuates in response to adjustments in generator output as well as removal and restoration of liquids (e.g., steam bubbles) from the tissue at the surgical site. The controller 24 monitors the tissue impedance and changes in tissue impedance and regulates the output of the generator 20 in response thereto to achieve the desired and optimal electrosurgical effect.

Figure 3:
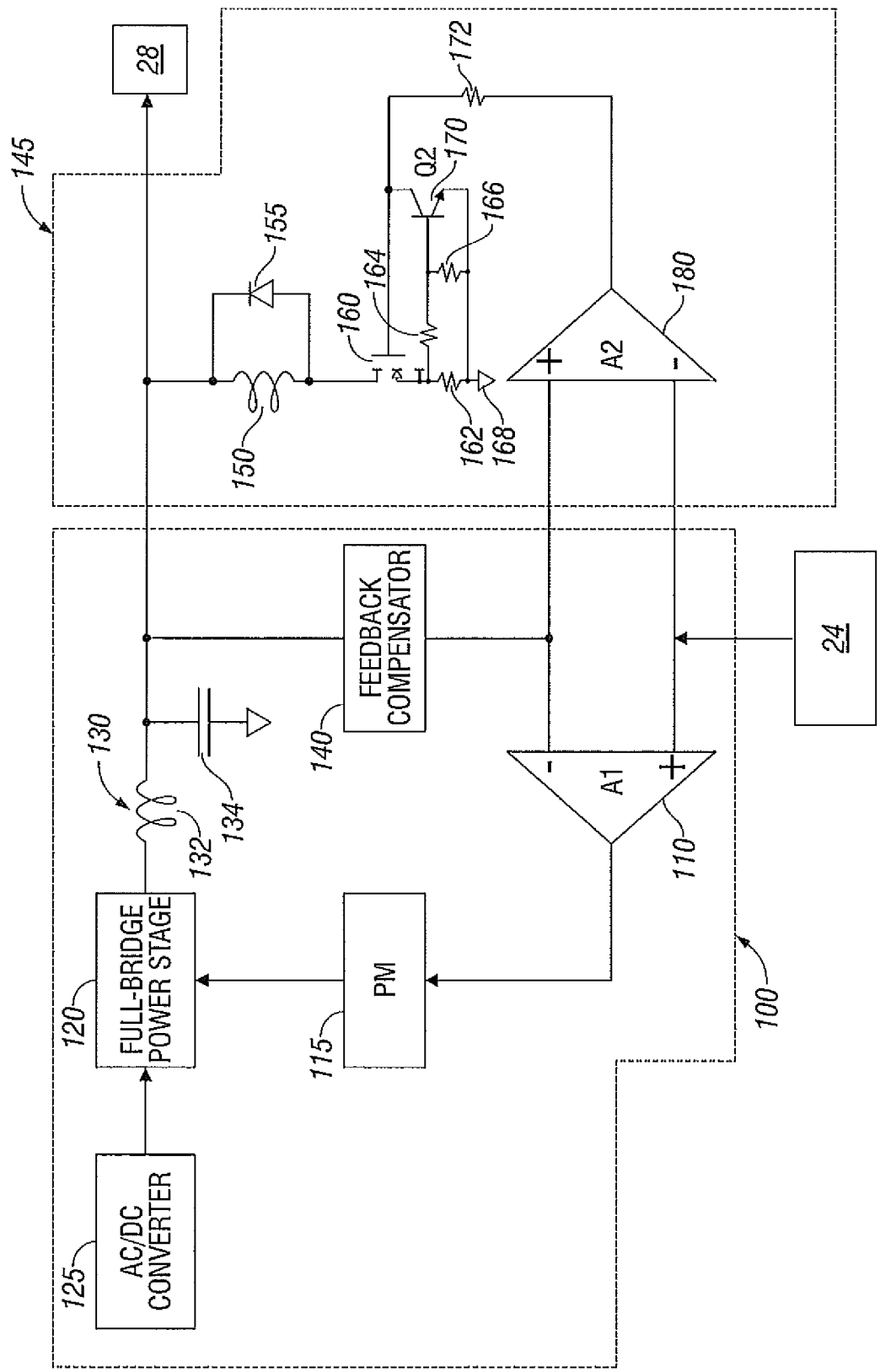
FIG. 3 is a circuit diagram of a power supply in accordance with an embodiment of the present disclosure.

Referring to FIG. 3, there is shown a block diagram of the power supply 27 including a control circuit 100 in series with a switching circuit 145. The control circuit 100 includes a first comparator 110 (e.g., an operational amplifier) having positive and negative input pins +A1 and −A1, respectively. Positive input pin +A1 is configured to receive an applied control signal (e.g., a variable DC voltage) from the controller 24 based on any one or more tissue parameters provided by the sensor module 22. Negative input pin −A1 is configured to receive a proportionally scaled feedback voltage of the power source output (e.g., connected to the RF output stage 28) to match the applied control signal on input pin +A1, as will be discussed in further detail below.

When the power source output fails to match the applied control signal, the resulting voltage difference at positive and negative input pins +A1 and −A1 causes the first comparator 110 to output an analog error signal (e.g., analog voltage) to drive a pulse modulator ("PM") 115. PM may be, for example, a pulse width modulator, a phase shift modulator or any such device known in the art for converting the analog error signal to a digital pulse control signal. The PM 115 converts the analog error signal to a digital pulse control signal (e.g., digital voltage) to implement control of a full-bridge power stage 120 by phase shifting the switching of one half-bridge with respect to the other. It allows constant frequency pulse-width modulation to provide high efficiency at high frequencies and can be used either as a voltage mode or current mode controller. More specifically, an AC/DC converter 125 converts an available ac signal (e.g., from an ac line voltage) to a dc signal to drive the full-bridge power stage 120, the output of which is, in turn, controlled by the digital pulse control signal to reflect the applied control signal from the controller 24. The resulting controlled output of the full-bridge power stage 120 drives an output filter 130 (e.g., a low-pass filter), having an inductor 132 and an output capacitor 134, to generate a DC output voltage V, across the output capacitor 134. The resulting output voltage V, is converted to RF energy by the RF output stage 28 and output to the electrosurgical instrument. A feedback compensator 140 continuously monitors the output voltage V, (e.g., input to the RF output stage 28) and, in turn, provides a proportionally scaled feedback of the power source output to input pin −A1 of the first comparator 110 to match the applied control signal from the controller 24.

With continued reference to FIG. 3, discharging of energy is achieved in real-time using an active discharge circuit (ADC) 145—a component of the power supply 27—that switches inductor 150 using a first switching component 160 in parallel with the output capacitor 134 to discharge the energy therefrom, as will be discussed in further detail below. The ADC 145 includes a second comparator 180 (e.g., an operational amplifier) having negative and positive input pins −A2 and +A2 operably coupled to the positive and negative input pins +A1 and −A2 of the first comparator 110, respectively. In this manner, the input pins −A2 and +A2 of the second comparator 180 continuously monitor the difference between the applied control signal from the controller 24 on positive input pin +A1 and the proportionally scaled feedback of the power source output on negative input pin −A1.

An inductive load 150 (e.g., an inductor) is connected in parallel with the output filter 130 and in series with the first switching component 160. The first switching component 160 is normally off and may be a transistor, such as a field-effect transistor (FET), metal-oxide semiconductor field-effect transistor (MOSFET), insulated gate bipolar transistor (IGBT), relay, or the like. A first resistive element 162 is in series with the first switching component 160 and with ground 168, which is known as a source follower circuit. The source follower limits the amount of current that flows through the first resistive element 162, the switching component 160, and the inductor 150.

In the case of the power source output being greater than the applied control signal (i.e., −A1>+A1), the switching circuit 145 utilizes inductive energy transfer to rapidly redirect the stored output energy of the power source 27 away from the RF output stage 28 until the power source output matches the applied control signal (i.e., −A1=+A1). More specifically, the second comparator 180 provides a drive voltage sufficient to close the first switching component 160 to discharge the stored energy from the output capacitor 134 to the inductive load 150. The activation of the first switching component 160 causes a conduction current $I_{Q1}$ to discharge from the capacitor 134 to ground 168 through the inductive load 150 and the first resistive element 162 to generate corresponding voltages $V_{Lr}$ and $V_{R1}$, respectively. That is, while the first switching component 160 is switched on, the inductive load 150 absorbs the energy discharged by the output capacitor 134 to rapidly decrease the output voltage $V_c$ until the power source output again matches the applied control signal (i.e., −A1 =+A1). Under this match condition, the second comparator 180 no longer provides the sufficient drive voltage, resulting in the first switching component 160 to return to the normally off position to interrupt the flow of the conduction current $I_{Q1}$ through the inductive load 150. The interruption of current flow through the inductive load 150 causes the magnetic flux field on the inductive load 150 to collapse due to a back electromagnetic force of voltage thereacross (e.g., a so-called "back EMF effect"). The back EMF voltage turns on diode 155, connected in shunt with the inductive load 150, to become forward-biased, providing a path for the inductor 150 magnetic flux and conductive current to be reset to zero. In addition this process prevents the back EMF voltage from increasing to a level sufficient to cause damage and/or stress to other components of the ADC 145 (e.g., the first switching component 160, the first resistive element 162, etc.).

The ADC 145 includes a second normally off switching component 170 that provides so-called "turn-on limiting" of the first switching component 160 to control the flow of the conduction current $I_{Q1}$ through the inductive load 150. More specifically, the second switching component 170 operates to monitor the voltage drop $V_{R1}$ across the first resistive element 162 caused by the conduction current $I_{Q1}$. Resistors 164 and 166 establish the threshold for component 170 turn on limiting. As the conduction current $I_{Q1}$ through the first switching component 160 increases, the voltage drop $V_{R1}$ across the first resistive element 162 increases to drive the second switching component 170 on, when the threshold for turn on limiting of component 170 is reached. The turn on of the second switching component 170 effectively reduces the drive voltage applied to the first switching component 160 to a steady state value from the second comparator 180, thereby regulating the current flow through the first switching component 160. The resulting reduced drive voltage of the first switching component 160 stabilizes the flow of conduction current $I_{Q1}$ through the first switching component 160 and, thus, through the first resistive element 162 thereby regulating the voltage drop $V_{R1}$ thereacross. In this manner, the output voltage $V_c$ across the output capacitor 134 discharges at an incremental time rate of change, represented by equation (1) below:

$$Vc = 1/C * \int_0^t I_{Q1} dt \qquad (1)$$

Where:

Vc is the output voltage across the capacitor 134;

C is the capacitance of the capacitor 134; and $I_{Q1}$ is the conductive current through the inductive load 150.

In the illustrated embodiment, one or more resistive elements 164 and 166 are utilized to set the desired proportion of the voltage drop $V_{R1}$ across the first resistive element 162 sufficient to turn on the second switching element 170. That is, each of resistive elements 164 and 166 may be interchanged with resistive elements of various resistance values to vary the proportion of the voltage drop $V_{R1}$ across the first resistive element 162 at which the second switching component 170 turns on. For example, the resistance ratio provided by the combination of the resistive elements 164 and 166, adjusts the proportion of the voltage drop $V_{R1}$ necessary to turn on the second switching component 170. The resistive elements 164 and 166 of FIG. 3 are illustrative only in that a single resistive element (not explicitly shown) or, alternatively, a plurality of resistive elements (not explicitly shown) in parallel and/or in series may replace the resistive elements 164 and 166 between the first switching component 160 and the second switching component 170 to achieve substantially the same purpose.

A buffer 172 (e.g., one or more resistors) between the first switching component 160 and the output of the second comparator 180 provides an isolation buffer therebetween when the second switching component 170 is turned on. As seen in FIG. 3, absent the buffer 172, the output of the second comparator 180 is shorted to ground 168 due to the closure of the second switching component 170. In this way, the buffer 172 operates to prevent a so called "over current" condition on the second comparator 180 during the closure of the second switching component 170.

Figure 4:
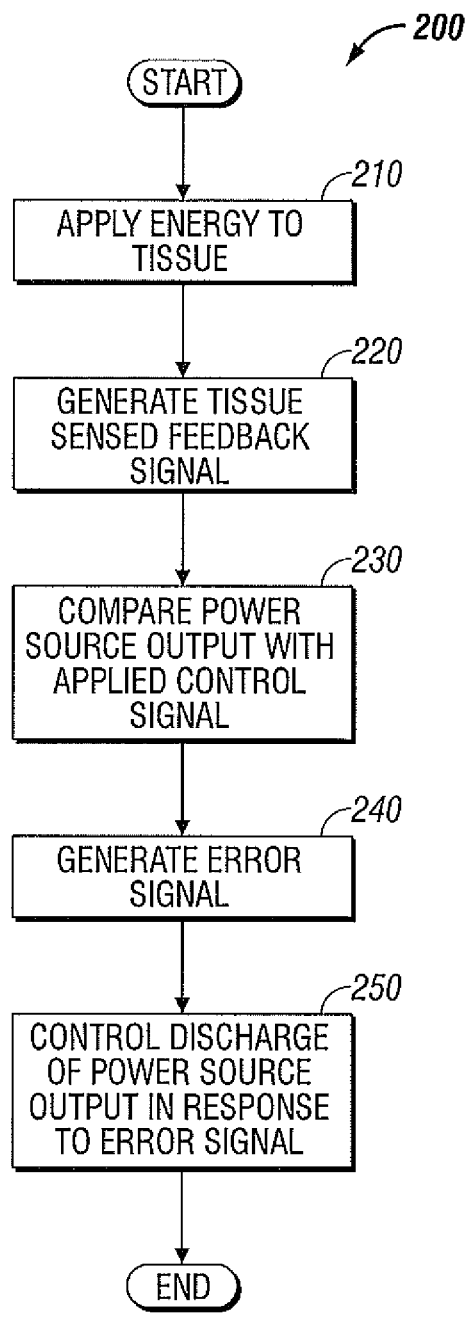
FIG. 4 is a flow chart diagram of a method for controlling the discharge of energy stored in an output of an electrosurgical generator according to an embodiment of the present disclosure.

FIG. 4 illustrates a method 200 for controlling the discharge of energy stored in an output of an electrosurgical generator. In step 210, energy is supplied to tissue. More specifically, the power supply 27 provides DC power to the RF output stage 28. The RF output stage 28 converts the DC power into RF energy and delivers the RF energy to tissue (e.g., via forceps 10). In step 220, the sensor module 22 generates a feedback signal to the controller 24 based on any one or more sensed tissue and/or energy properties. In step 230, a comparison is made between a control voltage generated by the controller 24 in response to the sensor feedback signal and the output voltage $V_c$ sampled by feedback compensator 140. In step 240, based on the comparison of step 230, an error signal is generated by the first comparator 110 and provided to the PM 115. PM 115 drives the full bridge power stage 120 to develop the output voltage Vc on capacitor 134, based on any one or more sensed tissue and/or energy properties. In step 250, the switching circuit 145 controls the discharging of the output capacitor 134 by redirecting the power supply 27 stored energy using the inductive load 150 in response to a reduction of required RF energy delivered to the tissue, based on any one or more sensed tissue and/or energy properties. Sensor module 22 provides feedback to controller 24 regarding the reduced RF energy need, whereby controller 24 then communicates a reduced control voltage to the power supply 27. Comparator 180 automatically monitors the reduced control voltage, where −A2 is now less than +A2, to drive switch 160 on. The turn on of switch 160 redirects the stored energy of output capacitor 134. As a result, the redirected stored energy in the power supply 27 lowers the output voltage Vc and rapidly reduces the delivered RF energy of the RF output stage 28.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A generator for providing treatment energy to tissue, comprising:

a power supply having an output filter and a discharge circuit, the output filter configured to store and output direct current energy;

an output stage coupled to the power supply and configured to convert the direct current energy into treatment energy for use in treating tissue; and a controller configured to adjust at least one of the power supply or the output stage to control the amount of treatment energy output by the output stage, wherein the discharge circuit is configured to control a time rate change of a discharge of the direct current energy stored in the output filter away from the output stage based on a comparison between the direct current energy stored in the output filter and a feedback signal generated by application of the treatment energy to tissue.

2. A generator for providing treatment energy to tissue according to claim 1, wherein the feedback signal is based on at least one sensed tissue property.

3. A generator for providing treatment energy to tissue according to claim 2, wherein the at least one sensed tissue property is derived based on an application of treatment energy output by the output stage to tissue.

4. A generator for providing treatment energy to tissue according to claim 2, wherein the at least one sensed tissue property is an increase in tissue impedance based on tissue desiccation.

5. A generator for providing treatment energy to tissue according to claim 1, further comprising a sensor operably coupled to the controller and configured to sense at least one tissue property.

6. A generator for providing treatment energy to tissue according to claim 5, wherein the feedback signal is generated by the sensor based on the at least one sensed tissue property.

7. A generator for providing treatment energy to tissue according to claim 1, wherein the output filter is an LC circuit.

8. A generator for providing treatment energy to tissue according to claim 1, wherein the treatment energy is RF energy.

9. A generator for providing treatment energy to tissue according to claim 1, wherein the controller is configured to adjust at least one of the power supply or the output stage to control the amount of treatment energy output by the output stage in real time.

10. A generator for providing treatment energy to tissue, comprising:
   a power supply having an output filter and a discharge circuit, the output filter configured to store and output direct current energy;
   an output stage coupled to the power supply and configured to convert the direct current energy into treatment energy for use in treating tissue;
   at least one sensor configured to sense at least one tissue property based on the application of treatment energy to tissue and configured to generate a feedback signal based on the at least one sensed tissue property; and
   a controller operably coupled to the at least one sensor and configured to adjust at least one of the power supply or the output stage to control the amount of treatment energy output by the output stage, wherein the discharge circuit is configured to provide time rate control of the discharge of the direct current energy stored in the output filter away from the output stage based on a comparison between the direct current energy stored in the output filter and the feedback signal generated by the sensor.

* * * * *